(12) United States Patent
Causey, III

(10) Patent No.: US 6,330,474 B1
(45) Date of Patent: Dec. 11, 2001

(54) ANNUNCIATOR FOR IMPLANTABLE SYSTEM

(75) Inventor: James D. Causey, III, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/236,967

(22) Filed: Jan. 25, 1999

(51) Int. Cl.[7] .................................................. A61N 1/39
(52) U.S. Cl. .................................................. 607/5; 607/27
(58) Field of Search .................................. 607/4, 5, 9, 27, 607/31, 32, 60

(56) References Cited

U.S. PATENT DOCUMENTS

| | | | |
|---|---|---|---|
| 3,319,201 | 5/1967 | Coen ..................................... 335/231 |
| 3,783,877 | * 1/1974 | Bowers ............................. 128/419 P |
| 3,886,419 | 5/1975 | Omura et al. . |
| 3,965,377 | 6/1976 | Carbonneau . |
| 4,086,916 | * 5/1978 | Freeman et al. ................ 128/2.05 T |
| 4,088,139 | * 5/1978 | Auerbach ....................... 128/419 PT |
| 4,102,346 | * 7/1978 | Fulker .............................. 128/419 PS |
| 4,210,149 | * 7/1980 | Heilman et al. ......................... 607/5 |
| 4,295,474 | * 10/1981 | Fischell ................................ 128/697 |
| 4,345,603 | * 8/1982 | Schulman ....................... 128/419 PT |
| 4,407,289 | * 10/1983 | Nappholz et al. ............. 128/419 PG |
| 4,494,022 | * 1/1985 | Kawara et al. ......................... 310/14 |
| 4,649,359 | 3/1987 | Doki et al. . |
| 5,076,272 | * 12/1991 | Ferek-Petric .................. 128/419 PG |
| 5,190,034 | * 3/1993 | Sholder ......................... 128/419 PG |
| 5,624,376 | * 4/1997 | Ball et al. .............................. 600/25 |
| 5,653,735 | * 8/1997 | Chen ........................................ 607/9 |
| 5,745,019 | * 4/1998 | Renger ................................. 335/222 |

* cited by examiner

Primary Examiner—George R. Evanisko

(57) ABSTRACT

An annunciator is provided for an organ stimulating system which is implantable in the body of a patient. A stimulus signal generator such as an implantable cardioverter defibrillator which includes an energizing capacitor is encased in a housing for imparting an electrical stimulation signal to an organ, such as a heart, to be stimulated. The signal generator includes a sensor for sensing at least one of a plurality of physiological characteristics and apparatus for generating an electrical signal corresponding to the sensed physiological characteristic. A vibration generator responsive to that electrical signal is then operable to impart to the housing a subaudible vibration, that is, one having a frequency less than about 250 hertz, which is detectable by the patient. The vibration generator may include, for example, a motor having an offset mass, a battery for driving the motor with the offset mass to thereby cause the vibrating effect, and a switch responsive to the electrical signal corresponding to the sensed physiological characteristic for electrically connecting the battery to the motor, energizing the motor, and thereby imparting the subaudible vibration to the housing.

13 Claims, 4 Drawing Sheets

ANNUNCIATOR FOR IMPLANTABLE SYSTEM

FIELD OF THE INVENTION

The present invention relates to annunciator devices for organ stimulating systems implantable in the body of a patient, and in particular, to such devices which may be used in combination with implantable defibrillator systems, for example, and be assured of attracting the attention of the patient upon the occurrence of a predetermined event. Still more particularly, the invention serves to produce a subaudible vibration which is detectable by the patient.

BACKGROUND OF THE INVENTION

Implantable defibrillation systems are known in the art which deliver a high-voltage defibrillation pulse to the heart when the onset of fibrillation is detected and/or in the event of a detected complete loss of cardiac output. Such known devices are also capable, if the heart exhibits an arrhythmia such as atrial fibrillation, atrial flutter or tachycardia, or ventricular tachycardia, of cardioverting the heart by delivering a high-voltage pulse in an attempt to regain synchronous operation of the heart, instead of delivering the higher voltage defibrillation pulse.

The disclosures of the following patents broadly present the current state of the art with respect to heart monitoring systems.

For example, it is known from U.S. Pat. No. 4,086,916 to contain a cardiac monitoring system in a wristwatch worn by a patient, the system including circuitry for detecting an erratic heartbeat, a missing pulse or other irregularities and providing an alarm indication, audio and visual, when such an event is detected.

It is also known from U.S. Pat. No. 4,088,139 to provide, in an implantable cardiac pacing system, means for generating a marking pulse in the pacemaker monitoring system if an event such as loss of capture occurs. The patient is not immediately informed of the occurrence of such an event, however, the system is provided with telemetry means so that when the recorded data is subsequently read out and examined by a physician, the data will include the marker indicating that loss of capture has occurred. The physician can then take such corrective steps as may be necessary.

An implantable pacing system is disclosed in U.S. Pat. No. 4,102,346 which includes an alarm device as part of the implanted unit which generates an alarm signal to inform the pacemaker user when the battery source of power of the pacemaker is nearing end of life or is malfunctioning.

An implantable tissue stimulating device is disclosed in U.S. Pat. No. 4,345,603 which activates an alarm which informs the patient in whom the system is implanted that the battery is in need of replacement. After the user has been so informed, the user applies a magnet externally in the vicinity of the implanted unit to deactivate the monitoring system and thereby cease the continued operation of the alarm.

A pacemaker for controlling tachycardia is disclosed in U.S. Pat. No. 4,407,289 also disclosing means for informing a pacemaker user of the remaining battery life. The user places a magnet externally in the vicinity of the implanted unit, which thereby causes the implanted unit to generate two pulses which can be seen on the patient's ECG waveform. The time separation between the two pulses indicates the remaining battery potential. Application of the magnet, after the pulses have been generated, temporarily disables the device.

In U.S. Pat. No. 5,190,034, an implantable arrhythmia treatment system is disclosed which includes reliable protection against the release of unneeded treatment pulses, that is, which provides protection against a false-positive output. The disclosed system utilizes an alarm generator which may be disposed in the implanted unit, or in an external unit. The alarm may be of any type which does not require constant, active monitoring by the user, such as a sensory alarm, for example, an audio alarm generator or a tactile alarm generator or "tickler".

Other examples of implantable arrhythmia devices which include an alarm generator, either audio, tactile, or visual, are found in U.S. Pat. Nos. 4,295,474; 4,210,149; and 3,783,877.

According to the current state of the art, error conditions are announced within an implantable cardioverter defibrillator (ICD) using a piezo annunciator or beeper. Some current implantable devices utilize a piezo actuator to flex the titanium can at audio frequencies. However, the efficacy of audio emissions from devices implanted abdominally can be questioned. The attenuation of the audio transmitted through tissue is dramatic. Aged patients commonly have hearing loss that further decreases their sensitivity to implanted audio generators.

As ICD design targets pectoral implantation, the ICD package dimensions decrease. A current example is the Jewel ™ ICD manufactured and sold by Medtronic Inc. of Minneapolis, Minn. The typical implementation of a piezo annunciator adds to the ICD thickness dimension. The Jewel™ ICD lacks an annunciator. Device malfunction, however, is not announced to the patient until the next scheduled follow-up.

It was in light of the foregoing that the present invention was conceived and has now been reduced to practice.

SUMMARY OF THE INVENTION

According to the invention, an annunciator is provided for an organ stimulating system which is implantable in the body of a patient. A stimulus signal generator such as an implantable cardioverter defibrillator which includes an energizing capacitor is encased in a housing for imparting an electrical stimulation signal to an organ, such as a heart, to be stimulated. The signal generator includes a sensor for sensing at least one of a plurality of physiological characteristics and apparatus for generating an electrical signal corresponding to the sensed physiological characteristic or diagnostic event. A vibration generator responsive to that electrical signal is then operable to impart to the housing a subaudible vibration, that is, one having a frequency less than about 250 hertz, which is detectable by the patient. The vibration generator may include, for example, a motor having an offset mass, a battery for driving the motor with the offset mass to thereby cause the vibrating effect, and a switch responsive to the electrical signal corresponding to the sensed physiological characteristic or diagnostic event for electrically connecting the battery to the motor, energizing the motor, and thereby imparting the subaudible vibration to the housing.

One embodiment of the invention, when applied, for example, to an ICD which utilizes a cylindrical high voltage photoflash-type capacitor for its energization, may be implemented by means of a cylindrical motor having the following attributes:

the motor diameter does not exceed the diameter of the capacitor;

the motor thickness may be typically 6 mm or less;

the motor is packaged within the ICD at one end of a capacitor, effectively adding 1 mm to the length of the capacitor;

the motor contains an offset mass to cause the vibrating effect; and the motor is directly powered by a typical low-impedance LiSVO (lithium silver vanadium pentoxide) defibrillator battery through an appropriate switching means.

While a motor with an offset mass represents one embodiment of the invention, other acceptable vibration-producing expedients, for purposes of the invention, may be, for example, in one instance, a linear reciprocating motor and, in another instance, a hammer and anvil combination.

It is noteworthy that regardless of the particular manner in which the vibrations are produced, they are of an inaudible quality or nature, intended to be felt, not heard. The pathway for the communication of the vibrations to the patient, therefore, is by stimulating nerves in the skin and/or in the trunk of the body of the patient. The vibrations are not transmitted either through the air or through the patient's skeleton to the ear as would be done were the vibrations within an audible range. In this instance, the vibrations are inaudible, that is, have a frequency of less than about 250 hertz.

The present invention offers numerous advantages. In a first instance, it provides a novel annunciator device applicable to organ stimulating systems which are implantable in a patient's body. More particularly, the invention may be used in combination with implantable defibrillator systems, for example, and be assured of attracting the attention of the patient upon the occurrence of a predetermined event. Still more particularly, the invention serves to produce a sub-audible vibration which is detectable by the patient.

Additionally, hearing loss on the part of the patient does not affect that patient's detection of the ICD error condition.

Furthermore, state of the art motor technology facilitates the realization of the invention with little risk to the patient in whom it is to be implanted.

By reason of the invention, pectoral implantation will assure that low vibration forces will be transmitted with assurance of attracting the patient's attention.

The proposed motor construction is not susceptible to damage by the forces applied to the ICD and its housing. Furthermore, typical cylindrical photoflash capacitor diameters are more than adequate to permit the addition of the proposed motor without adding significantly to the ICD dimensions.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DESCRIPTION OF THE PREFERRED EMBODIMENTS

Figure 1:
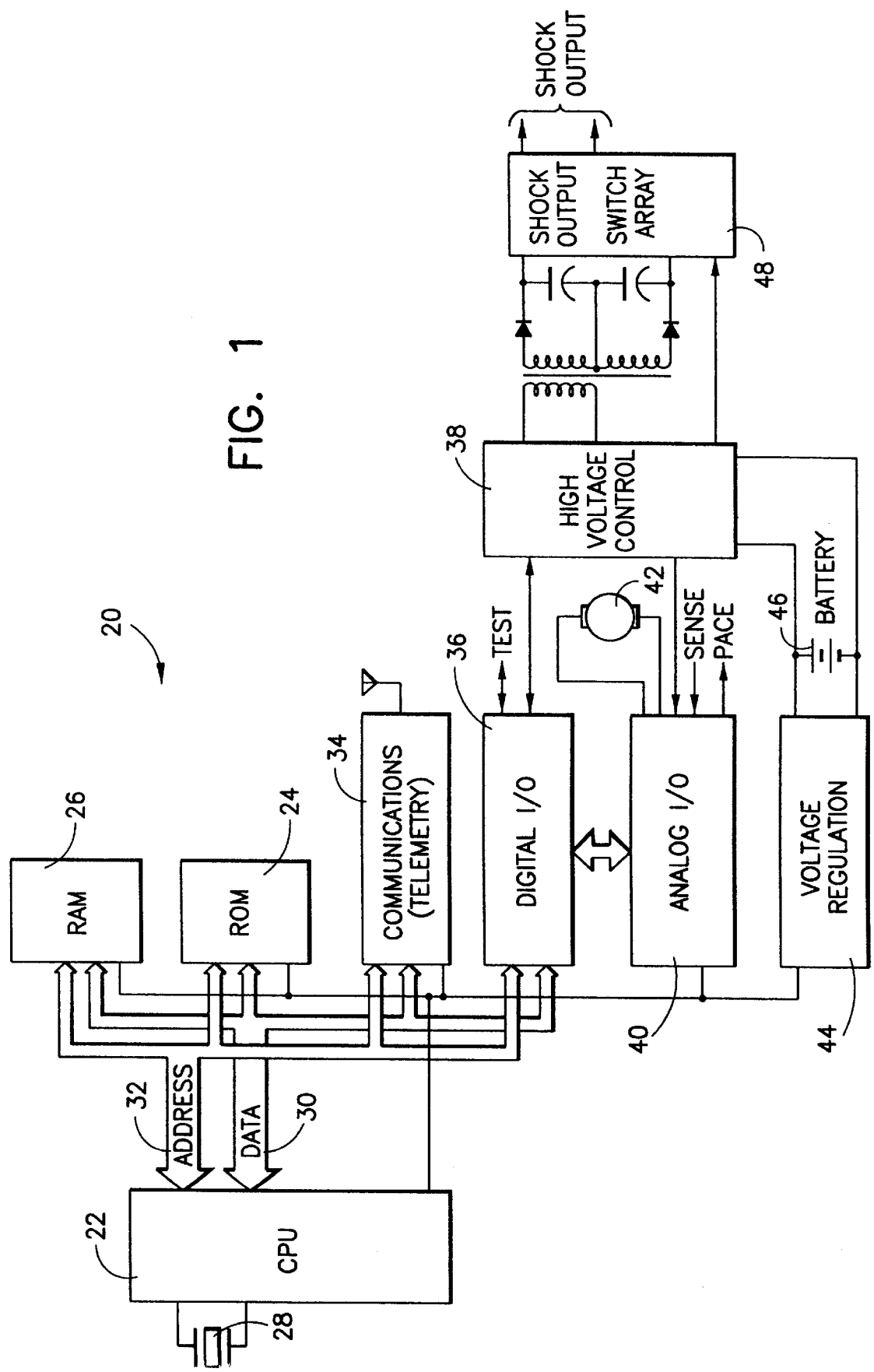
FIG. 1 is a schematic block diagram of an implantable cardioverter defibrillator (ICD) system constructed in accordance with the principles of the present invention.

Turn now to the drawings and, initially, to FIG. 1 which is a block diagram which schematically illustrates an implantable cardioverter defibrillator (ICD) system 20 constructed in accordance with the principles of the present invention. In the system 20, CPU 22 is the central processing unit and executes the ICD program that resides in ROM 24 and RAM 26. The CPU 22 is connected to a 32 kHz crystal 28 for the generation of low-frequency timing signals.

The CPU data and address busses 30, 32, respectively, connect the CPU 22 to various digital resources that comprise the ICD electronic system. The ROM 24 is read-only-memory and is programmed as the ROM integrated circuit is manufactured. The function of the ROM is analogous to a floppy disk for a personal computer that contains a software program; the binary data that the CPU 22 executes is, in effect, stored on the "floppy disk". The RAM 26 is random-access-memory and is used for storage of program variables, for the storage of intracardiac electrograms and other diagnostic data. The RAM also contains a portion of the ICD system program. During operation of the CPU 22, the contents of the RAM may be read or modified while the contents of the ROM may only be read.

A communications block 34 integrates analog and digital circuitry to facilitate bidirectional telemetry between the ICD system 20 and an external programmer through a very low-power proprietary radio-frequency link. A digital I/O module 36 interfaces additional electronic resources to the CPU 22. The digital I/O module converts the parallel data and address buses 30, 32 to a serially-interfaced high voltage control block 38 and to an analog I/O module 40. The analog I/O module contains circuitry to sense intracardiac activity and to pace the patient's heart to deliver pacing stimulation for anti-bradycardia and anti-tachycardia therapy. The analog I/O module additionally integrates circuit functions to measure the integrity of the pacing electrode connection to the patient's heart, to measure high voltages generated within the high voltage control block 38 and circuitry to power a vibratory motor, to be described, or other low-frequency vibration generating mechanism.

A voltage regulation block 44 stabilizes voltage from battery 46 for distribution to the various electronic blocks of the system 20. The high voltage control block 38 controls the conversion of the battery voltage (less than 7 volts) to more than 700 volts through the process of DC—DC conversion. The high voltage control block also controls the timing of a shock output switch array 48 that commutates the stored high voltage to the shock output connections to deliver to the patient a therapeutic high voltage shock.

The battery 46 serves as the energy source for all operations of the ICD system 20, including the operation of the vibratory motor 42 or other low-frequency vibration generating means.

There comes a time during the operation of the system 20 that it becomes necessary or desirable to notify the patient (wearer of the ICD) and/or the physician of the existence of an important operating condition which has come to pass. In some instances, ICDs have incorporated a piezo ceramic beeper assembly comprising a metallic disc with a piezo ceramic transducer bonded to the disk. The ICD electronics would apply an AC signal (at an audio frequency of interest) between the metallic disc and the available surface of the piezo ceramic transducer to cause the same to flex. Such notification may be signaled for any of the following, or other, reasons:

An ICD error condition might require a physician to replace or reprogram the ICD and the ICD sounds an error tone to cause the patient to communicate with the physician;

The ICD may vibrate to warn the patient that it is about to deliver a high energy shock so that the patient may sit, stop driving or otherwise prepare for a painful therapy event and stimulation of skeletal muscles;

The ICD may vibrate to warn the patient that the patient's heart rhythm is erratic and that the patient may be at risk of initiating a tacharrhythmia.

Figure 2:
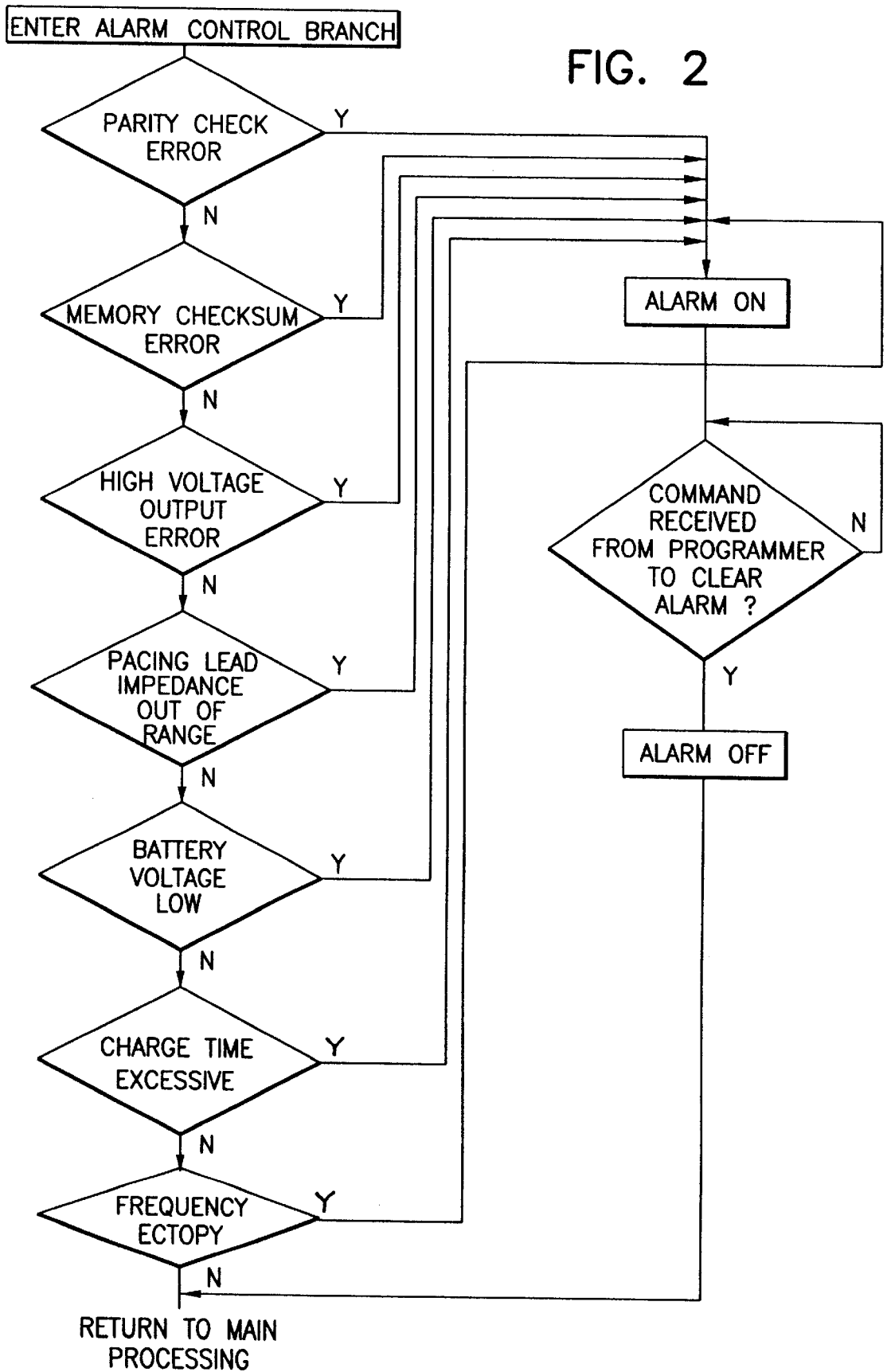
FIG. 2 is a schematic flow diagram presenting the alarm control sequence of operation for an ICD constructed in accordance with the principles of the present invention.

FIG. 2 is an operational flow diagram which presents a variety of conditions for which a signal is generated and the manner in which the system responds to each such signal. As seen in FIG. 2, there are many instances in which a condition would operate a suitable alarm. These instances include parity check error, memory checksum error, high voltage output error, pacing lead impedance out of range, battery voltage low, charge time excessive, and frequency ectopy. Operation of the alarm persists until such time that the condition has been attended to at which point the alarm is cleared and the organ stimulating system is returned to normal operation.

Figure 3:
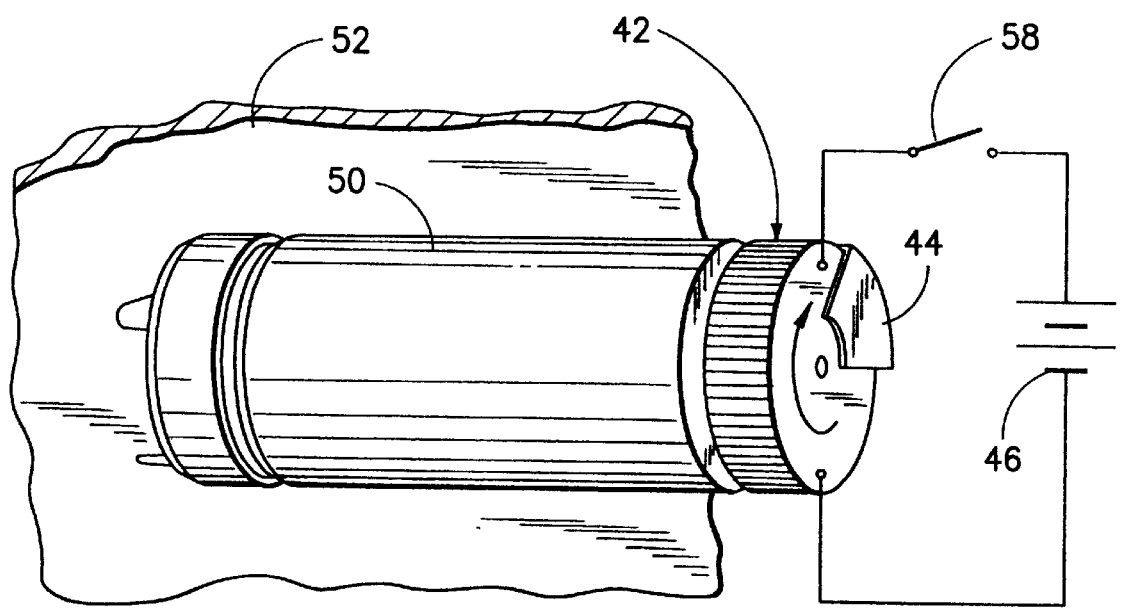
FIG. 3 is a diagrammatic view, partially perspective, of one embodiment of a vibration generator employed in accordance with the principles of the present invention.
Figure 4:
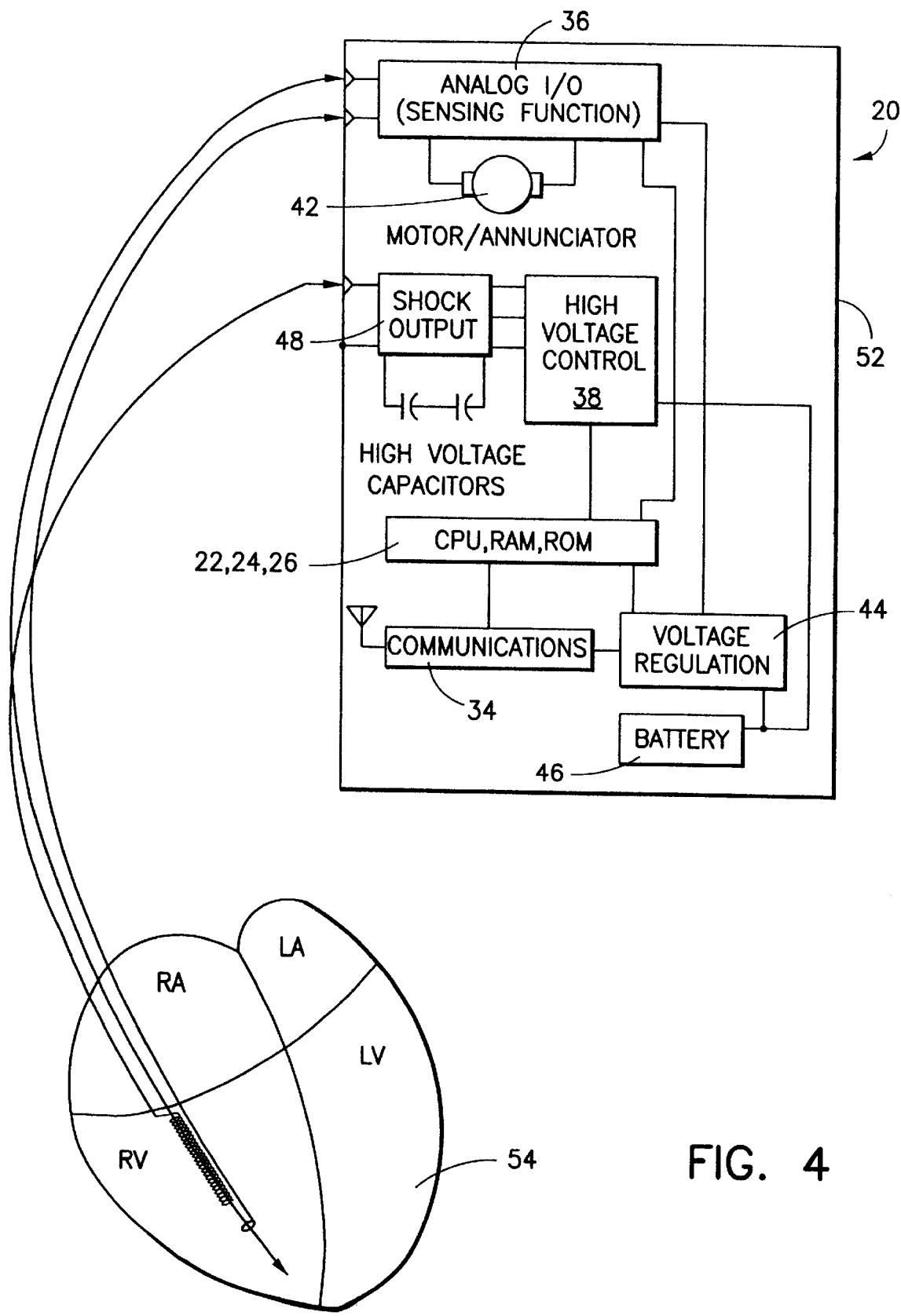
FIG. 4 is a diagrammatic view of the vibration generator of FIG. 3 as used with the ICD system of FIG. 1.

Viewing, now, FIGS. 1, 3 and 4, an organ stimulating system implantable in the body of a patient may be, for example, the ICD system 20 which includes a stimulus signal generator 50 encased in a housing 52 for imparting the electrical stimulation signal to an organ, typically heart 54, to be stimulated. The signal generator 50 includes a suitable sensor 36 for sensing at least one of a plurality of physiological characteristics and a signal generator 48 for generating an electrical signal corresponding to the sensed physiological characteristic. As seen in FIGS. 3 and 4, the stimulus signal generator is typically a cylindrical high voltage photoflash capacitor.

In accordance with the invention, the system 20 also includes a vibration generator which is responsive to the electrical signal corresponding to the sensed physiological characteristic for imparting to the housing 52 a subaudible vibration which is detectable by the patient. A subaudible vibration is defined as one having a frequency less than about 250 hertz. A typical construction of the vibration generator is illustrated in FIGS. 3 and 4 as the motor 42 and is depicted as being a cylindrical motor bonded to one end of the capacitor 50.

As seen particularly well in FIG. 3, the motor 42 has an offset mass 44 and is driven by the battery 46 to thereby cause the vibrating effect. A suitable switch 58 is responsive to an electrical signal corresponding to the sensed physiological characteristic for electrically connecting the battery to the motor, energizing the motor, and thereby imparting the subaudible vibration to the housing 52.

The motor 42 preferably has the following attributes:
motor diameter does not exceed the diameter of the cylindrical high voltage photoflash capacitor 50;
motor thickness may be typically 1 mm or less;
the motor 42 is packaged within the ICD system 20 at one end of the photoflash capacitor 50, effectively adding about 1 mm to the length of the capacitor;
the motor 42 contains an offset mass 44 to cause the vibrating effect; and
the motor 42 is directly powered by the typical low-impedance SVO defibrillator battery 46.

A typical motor may be Model No. 6 cv-1501WL-00 sold by Namiki Precision of America, Inc. of Rochelle Park, N.J.

Notwithstanding the foregoing, while a motor with an offset mass is one example of a vibration generator, it is the intent of the present invention to broadly cover any device or mechanism or method for generating a low frequency (that is, less than about 250 Hz) vibration of the implanted device to be sensed by the patient through vibration rather than in an audible way. In this regard, it is noteworthy that an ICD patient is commonly over 55 years of age and is likely to have experienced losses in audio frequency and amplitude with regard to hearing. The invention would serve ICD patients with complete loss of hearing as well as alert a sleeping patient.

Advantages which accrue from such a system as just described include the following:

1. patient hearing loss does not affect the patients' detection of an ICD error condition;
2. state of the art motor technology facilitates the realization of the goal sought with little risk to the patient;
3. pectoral implantation enables use of low vibration forces to attract the patients' attention;
4. the proposed motor is not susceptible to damage by forces applied to the housing for the ICD system; and
5. typical cylindrical photoflash capacitor diameters are more than adequate to permit the addition of the proposed motor without adding significantly to the ICD dimensions.

In recapitulation, it is the intent of the inventor that the present invention cover all implementations of annunciators that emit vibration that the patient does not receive audibly, the essence of the invention being to attract the attention of the patient without requiring the patient to hear an audible signal. The above disclosure is provided in that context.

Thus, while preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An organ stimulating system implantable in the body of a patient comprising:
   an implantable housing;
   a stimulus signal generator, encased in the housing, for imparting an electrical stimulation signal to an organ to be stimulated, the signal generator including a sensor for sensing at least one of a plurality of physiological characteristics and means for generating an electrical signal corresponding to the sensed physiological characteristic; and
   a vibratory motor responsive to the electrical signal corresponding to the sensed physiological characteristic for imparting to the housing a subaudible vibration which is detectable by the patient;
   wherein the vibratory motor includes:
   a motor having an offset mass; and
   a battery for driving the motor with the offset mass to thereby cause the vibrating effect.

2. The organ stimulating system, as set forth in claim 1, wherein the subaudible vibration imparted to the housing by the vibration generator has a frequency less than about 250 hertz.

3. The organ stimulating system, as set forth in claim 1
wherein the stimulus signal generator is an implantable cardioverter defibrillator including an energizing capacitor; and
wherein the vibratory motor further includes:
  switch means responsive to the electrical signal corresponding to the sensed physiological characteristic for electrically connecting the battery to the motor, energizing the motor, and thereby imparting the subaudible vibration to the housing.

4. The organ stimulating system, as set forth in claim 1
wherein the organ is a patient's heart;
wherein the stimulus signal generator delivers stimulation pulses to the patient's heart; and
including:
control means for controlling the stimulus signal generator in at least one of a plurality of modes; and
error detecting means, coupled to the control means, for detecting at least one of a plurality of possible errors of the implantable organ stimulating system.

5. The organ stimulating system, as set forth in claim 4, wherein the vibratory motor comprises:
  a drive means, coupled to the motor, for driving the motor with the offset mass; and
  switch means, responsive to the error detecting means, for electrically connecting the drive means to the motor, thereby energizing the motor which, in turn, imparts the subaudible vibration to the housing.

6. The organ stimulating system, as set forth in claim 5
wherein the drive means comprises a lithium silver vanadium pentoxide (LiSVO) battery switchably coupled to the motor.

7. The organ stimulating system, as set forth in claim 5, wherein the drive means comprises:
  a capacitor mechanically coupled to the motor; and
  wherein the battery is electrically coupled to the capacitor for charging the capacitor.

8. The organ stimulating system, as set forth in claim 7, wherein the capacitor comprises a high voltage photoflash capacitor.

9. The organ stimulating system, as set forth in claim 7, wherein the vibratory motor comprises a motor having a low-profile shape that is dimensioned to match one end of the capacitor.

10. The organ stimulating system, as set forth in claim 4, wherein the error detecting means comprises means for detecting errors of the implantable organ stimulating system.

11. The organ stimulating system, as set forth in claim 10, wherein the means for detecting errors comprises means for detecting at least one of parity check errors, memory checksum errors, high voltage output errors, pacing lead impedance out of range, battery voltage low, charge time excessive, and frequency ectopy.

12. The organ stimulating system, as set forth in claim 4, wherein the error detecting means comprises means for detecting an important operating condition.

13. The organ stimulating system, as set forth in claim 12, wherein the error detecting means comprises:
  means for detecting at least one of an error condition which may require a physician to replace or reprogram the organ stimulating system, an impending high energy shock so as to warn the patient, and the presence of a heart rhythm that is erratic and that the patient may be at risk of initiating a tacharrhythmia.

* * * * *